(12) United States Patent
Minor

(10) Patent No.: US 7,348,144 B2
(45) Date of Patent: Mar. 25, 2008

(54) METHODS AND SYSTEM FOR MULTI-DRUG TREATMENT DISCOVERY

(75) Inventor: James M. Minor, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 578 days.

(21) Appl. No.: 10/640,081

(22) Filed: Aug. 13, 2003

(65) Prior Publication Data

US 2005/0037363 A1 Feb. 17, 2005

(51) Int. Cl.
C12Q 1/68 (2006.01)
G01N 33/53 (2006.01)

(52) U.S. Cl. ............................ 435/6; 435/7.1; 977/791; 977/839

(58) Field of Classification Search ............... 435/6, 435/7.1; 977/791, 839
See application file for complete search history.

(56) References Cited

U.S. PATENT DOCUMENTS

| | | | |
|---|---|---|---|
| 5,860,917 A | 1/1999 | Comanor et al. | |
| 6,171,797 B1 | 1/2001 | Perbost | |
| 6,180,351 B1 | 1/2001 | Cattell | |
| 6,188,969 B1 | 2/2001 | Minor | |
| 6,222,664 B1 | 4/2001 | Dorsel | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,355,921 B1 | 3/2002 | Staton et al. | |
| 6,371,370 B2 | 4/2002 | Sadler et al. | |
| 6,406,849 B1 | 6/2002 | Dorsel et al. | |
| 6,486,457 B1 | 11/2002 | Dorsel et al. | |
| 6,518,556 B2 | 2/2003 | Staton et al. | |
| 2003/0049701 A1* | 3/2003 | Muraca | 435/7.23 |
| 2004/0053317 A1* | 3/2004 | Glinskii | 435/6 |

OTHER PUBLICATIONS

Paik, Molecular Profiling of Breast Cancer, Curr Opin Obstet Gynecol 18: 59-63 (2006).*
ExonHit Therapeutics presents at SG Cowen Annual Health Care Conference in Boston, pp. 1 of 2. Mar. 7, 2003. http://www.exonhit.com/index.php?page=219& PHPSESSID=k442jjk....
Thayer, Ann. M. Biomarkers Emerge, Chemical & Engineering News. vol. 81, No. 30, CENEAR 81 30, pp. 33-37, Jul. 28, 2003.

* cited by examiner

Primary Examiner—Mark L. Shibuya

(57) ABSTRACT

Methods, systems and recordable media for using expression data characterizing protein pathways of diseases to produce phase relationships between treatment responses of diseased tissues to treatments applied thereto and expression profiles of the diseased tissues as measured when untreated. Methods, systems and recordable media for augmenting an original or existing treatment or treatment combination with one or more treatments that cover gene activity of a disease not addressed by the original/existing treatment.

25 Claims, 8 Drawing Sheets

|  | Tissue Sample | | | | | | | | | | | |
|---|---|---|---|---|---|---|---|---|---|---|---|---|
|  | 1 | 2 | 3 | ∘ | ∘ | ∘ | ∘ | ∘ | ∘ | ∘ | ∘ | 60 |
| mRNA 1 | $x_{1,1}$ | $x_{2,1}$ | $x_{3,1}$ | | | | | | | | ∘ | $x_{1,60}$ |
| 2 | $x_{1,2}$ | $x_{2,2}$ | $x_{3,2}$ | | | | | | | | ∘ | $x_{2,60}$ |
| 60,000 | $x_{60,000,1}$ | $x_{60,000,2}$ | $x_{60,000,3}$ | | | | | | | | ∘ | $x_{60,000,60}$ |
| Treatments 1 | $Y_{1,1}$ | $Y_{1,2}$ | $Y_{1,3}$ | | | | | | | | ∘ | $Y_{1,60}$ |
| 70,000 | $Y_{70,000,1}$ | $Y_{70,000,2}$ | $Y_{70,000,3}$ | | | | | | | | ∘ | $Y_{70,000,60}$ |

400

| idrow | LC:NCI-H23 | LC:NCI-H226 | LC:A549/ATCC | LC:NCI-H322M | LC:EKVX | LC:NCI-H522 | LC:HOP-62 | LC:HOP-92 | Cluster | Distance | NSC or gene | Drug Name or gene |
|---|---|---|---|---|---|---|---|---|---|---|---|---|
| 328 | -0.111286623 | 0.178505063 | 0.149213850 | 0.375907987 | 0.646788657 | -0.0079102121 | 0.072614521 | -0.210706532 | 23 | 0.753208808 | | (4-Methoxyphenyl)-(3 |
| 1663 | -0.316399429 | 0.415162653 | 0.205730468 | 0.382667363 | 0.076958603 | -0.99984976 | 0.224805415 | 0.093632996 | 23 | 0.755556102 | 638484 | est |
| 2169 | -0.237350881 | 0.800352573 | 0.146478295 | 0.316387355 | 0.158144951 | -0.807192663 | 0.221313775 | 0.024145007 | 23 | 0.773565903 | "H.sapiens htbm mRNA" | |
| 2245 | 0.078998042 | 0.422789901 | 0.134431372 | -0.004957419 | 0.316234708 | -0.435221642 | -0.0716874 | 0.488718774 | 23 | 0.780488991 | "HSD3B1 Hydroxy-delta" | 691700 |
| 2106 | -0.140933037 | 0.461490691 | 0.499890865 | 0.298458338 | 0.120439963 | -1.042428613 | 0.307734688 | 0.010511637 | 23 | 0.794477643 | | 691700 |
| 2432 | -0.174853 | 0.112137318 | 0.077538596 | 0.389694452 | 0.178966765 | -1.131978273 | 0.22249597 | 0.092113219 | 23 | 0.804479103 | "SID 470501, ESTs" | est |
| 695 | -0.076172821 | 0.353985565 | -0.11117027 | 0.121181577 | -0.112142891 | 0.107680403 | 0.081476666 | -0.245336369 | 23 | 0.81949499 | "SID W 470610, Homo" | 698249 |
| 1338 | 0.168118119 | 0.051103168 | 0.184467409 | 0.210656643 | 0.462407589 | 0.048299193 | 0.316761762 | 0.179974934 | 23 | 0.84817046 | | 698249 |
| 1214 | -0.187852487 | 0.624020225 | 0.162335858 | 0.299287945 | 0.583450139 | -0.904382706 | 0.043432295 | -0.296958864 | 23 | 0.84980264 | "Homo sapiens GBAS" | est |
| 1365 | -0.333529115 | -0.343035513 | 0.195442408 | 0.301968051 | 0.255947471 | -0.809228301 | 0.225683933 | 0.031121492 | 23 | 0.87483881 | | 2013 | 10-Undecenoic-Servinon |
| 1981 | 0.064776063 | 0.687491974 | 0.013931334 | 0.598295523 | -0.096971869 | -0.909188867 | 0.225480229 | 0.279256523 | 23 | 0.88244174 | "SID W 488046, ESTs" | est |
| 1598 | 0.217021704 | 0.246318996 | 0.657769322 | 0.431177616 | -0.170978725 | -0.310296714 | 0.556480229 | -0.146480709 | 23 | 0.8892868 | "SID W 195336, Homo" | est |
| 1652 | -0.156265618 | 0.447149515 | 0.059461489 | 0.285014331 | 0.123365164 | -1.222979307 | 0.193187922 | 0.067459166 | 23 | 0.88994507 | "TXNRD1 Thioredoxin" | est |
| 1958 | -0.162251085 | 1.02794838 | 0.558362126 | 0.529456854 | 0.209431112 | -1.198800051 | 0.316675749 | 0.077234894 | 23 | 0.89170218 | "SID W 509612, CLEAVAGE" | est |
| 1646 | 0.117496537 | 0.562757611 | 0.073094208 | 0.35881573 | 0.264473051 | -0.264473051 | 0.63888061 | -0.031432077 | 23 | 0.90443955 | "ESTs Chr.4 (488622" | est |
| 1697 | -0.139905393 | 0.280929787 | -0.021258652 | 0.504650652 | -0.095209285 | -1.091620564 | 0.108648662 | -0.109391618 | 23 | 0.93060404 | "SID W 299059, ESTs" | est |
| 1395 | 0.647027731 | 0.574884869 | 0.293306006 | 0.441056967 | 0.601008022 | -0.554738343 | 0.204279572 | 0.483417749 | 23 | 0.96058997 | "SID W 510489, Transferrin" | est |
| 1456 | -0.134611617 | 0.574884869 | 0.156647593 | 0.251265675 | 0.413924575 | 0.348856398 | 0.49960196 | 0.119401693 | 23 | 0.96629182 | "TISSUE FACTOR PATHWAY INHIBITOR" | est |
| 2425 | -0.414396763 | -0.186291218 | 0.275927961 | 0.280380845 | 0.346750743 | -1.120622158 | 0.307901472 | 0.105654359 | 23 | 0.96821561 | "ESTs, Weakly similar to GAP22 protein" | est |
| 2782 | -0.103623688 | 0.187982798 | -0.699450089 | -0.081969425 | 0.002358456 | -0.433278124 | 0.657848206 | 0.176251769 | 23 | 0.97242958 | | 656156 |
| 2777 | 0.443294168 | 0.254137874 | -0.518829286 | 0.139691621 | 0.083881853 | -0.897575855 | 0.541921735 | 0.29845645 | 23 | 0.98045556 | "GLRX Glutaredoxin" | est |
| 2219 | -0.222163931 | 0.355980694 | -0.613482475 | 0.406674802 | 0.187242478 | -0.056112427 | 0.09599209 | -0.265899019 | 23 | 1.00044521 | "SID 35316, ESTs [5':R24770, 3':RA5303]" | 656156 |

Fig. 5A

| | 501 | 502 | 503 | 504 | 505 | 506 | 507 | 508 | 509 | 510 | 511 | 518 | 519 |
|---|---|---|---|---|---|---|---|---|---|---|---|---|---|
| 1035 | 0.59174782 | -0.472057058 | 1.049650941 | -0.130432069 | -0.042563555 | -1.090800844 | -0.308516371 | -0.85551703 | 23 | 201340786 | | | 642049 |
| 2485 | -1.017101288 | 0.551484346 | -0.417378098 | -0.374083847 | 0.344193816 | 0.992566109 | 0.143580616 | 0.360326648 | 23 | 201541842 | "Homo sapiens cyclin-dependent | | est |
| 2067 | -0.128467411 | 0.128146335 | -0.671163261 | 0.074424088 | 0.17572777 | 1.365454435 | 0.811493158 | 0.304440498 | 23 | 201613372 | "SID W 415061, ESTs | | est |
| 1977 | -0.736096203 | 0.284860611 | -0.461407721 | -0.194372892 | -0.295665324 | -1.580191374 | 0.178860595 | -1.072011828 | 23 | 201719192 | "SID W 417320, Plasminogen activator | | est |
| 2520 | 0.067721359 | 1.80341351 | 0.508630693 | 0.295597707 | 1.071573053 | 0.177196115 | 0.958690047 | 0.265765965 | 23 | 201865206 | "SID 201350, ESTs [5':R99701, 3':R99396]" | | est |
| 1827 | -0.197292775 | -0.911904454 | 0.66439967 | 0.121587418 | -0.576198895 | -0.238213527 | -0.247811511 | -1.126745462 | 23 | 201964736 | "Human fetus brain mRNA | | est |
| 2095 | 0.03913632 | 0.629996419 | 1.912577629 | 0.281426251 | 0.787353992 | -0.466889894 | 0.052946653 | -0.457666963 | 23 | 201988567 | "INTERLEUKIN-1 RECEPTOR, TYPE I | | est |
| 1809 | -1.079775572 | -0.041749958 | -0.039842077 | -0.180696249 | -0.30931738 | -0.624570191 | 0.695960045 | 1.547246333 | 23 | 202059792 | "SID 344786, Human mRNA | | est |
| 1367 | -0.238405168 | 0.037147382 | -0.141207382 | 0.65131557 | -1.624247193 | -0.037735999 | 0.078842044 | 0.5826419 | 23 | 202107778 | "Homo sapiens KIAA0429 mRNA | | est |
| 1493 | 0.069943645 | 0.4572049 | -0.175981224 | -0.964397073 | 0.550413191 | -0.222506791 | 1.605974674 | -0.885804892 | 23 | 202160965 | "SID W 494681, Homo sapiens ES/130 | | est |
| 491 | -0.271484077 | 0.919035547 | 1.558635626 | -0.587312162 | 0.043116227 | -0.709985018 | 1.087688804 | 0.577217162 | 23 | 202189107 | | 301739 | Mitoxantrone |
| 2277 | 0.842014479 | -0.594415665 | 0.760551155 | 0.280265689 | -0.370500267 | -0.026089132 | -0.733894871 | -0.664064944 | 23 | 202192883 | | 272346 | 1-Piperazinecarbothioic |
| 2635 | 0.327130854 | 2.041123567 | 0.203182548 | 0.345517129 | 0.097729474 | -0.477246881 | 0.316134542 | 0.888397117 | 23 | 202290294 | | 374998 | est |
| 96 | 0.661729097 | 0.40828824 | 0.484313488 | 1.347993016 | 0.18526336 | -0.404236674 | 0.405760497 | -1.490653396 | 23 | 202341173 | "SID W 376416, Complement | | est |
| 1938 | -0.363292009 | 1.737147639 | -0.276968539 | -0.002954174 | 0.160331607 | -0.945163177 | 0.311912924 | 1.104579806 | 23 | 202376721 | "MT1L Metallothionein | | est |
| 907 | 0.827655011 | 1.089080095 | -0.042288482 | -0.062037909 | -1.090178407 | 0.066714676 | 0.45596518 | 0.039990805 | 23 | 202405693 | | 640322 | [(Aminomethyl)(2-aminoethyl)am |
| 1863 | -0.550456226 | -0.856063276 | -0.288816678 | 0.03772549 | -0.506671309 | -0.784143896 | 1.218905807 | 1.128417611 | 23 | 202472796 | "SID W 322138, Hexokinase | | est |
| 696 | -0.885003915 | -0.669573545 | -0.090716049 | 0.704339385 | 0.56654799 | -1.79099226 | 0.836082757 | 0.028836638 | 23 | 202484619 | | 662825 | 662825 |
| 2616 | -0.544181049 | 0.006849032 | 0.289357616 | 0.714302421 | 0.035633717 | 0.580322385 | -0.281256627 | -1.37290132 | 23 | 202503219 | "ESTs Chr.19 [124956 | | est |
| 2642 | -0.256247163 | 0.573804379 | 0.807493687 | 0.249306053 | 0.419947876 | -1.996891737 | 0.0911621 | 0.913210809 | 23 | 202600874 | "SID 277268, ESTs [5'; 3':N34396]" | | est |

| | 501 | 502 | 503 | 504 | 505 | 506 | 507 | 508 | 509 | 511 | 510 | 518 | 519 | |
|---|---|---|---|---|---|---|---|---|---|---|---|---|---|---|
| 2539 | -0.110114709 | 0.623301029 | -0.147871226 | 0.214629188 | 0.126499416 | 0.728118777 | 0.022603825 | -2.705047131 | | 23 | 3.04925062 | "ESTs SID 47970, [5':H12268, 3':]" | | est |
| 2178 | -0.501060545 | 0.923337221 | -0.361292392 | -0.792244315 | -0.800491733 | -0.535742164 | -0.415886637 | -2.287745476 | | 23 | 3.04942806 | "SID W 489262, Allograft inflammatory factor 1 | | est |
| 676 | 2.256357431 | 0.662154436 | 0.576992869 | 1.257008805 | -0.591802716 | -0.915100771 | 0.105959946 | -1.358154058 | | 23 | 3.05417812 | | 645735 | 1 |
| 2349 | 1.017841697 | -2.006494761 | -0.333019529 | -0.710412264 | -0.479137897 | 0.514294386 | -0.315817654 | 0.558562398 | | 23 | 3.054701709 | "ESTs, Highly similar to ABC1 PROTEIN | | est |
| 1019 | -1.216163186 | 0.924963792 | -1.160476327 | -0.499548884 | -0.176264644 | 0.787338614 | -0.741926908 | 1.49763608 | | 23 | 3.05530722 | | 651593 | 651593 |
| 897 | 0.229729205 | -0.262540638 | -0.151262417 | 0.399956703 | -2.618956089 | 0.470789433 | -0.105083197 | 0.386281252 | | 23 | 3.05611789 | | 352277 | COLCHICIDE.HCL |
| 604 | 0.086529441 | 0.249568282 | 0.288641036 | 0.75741607 | -1.034515381 | 0.316785216 | 0.222775102 | -2.615675688 | | 23 | 3.05597948 | | 125973 | Paclitaxel—Taxol |
| 1250 | 0.139398472 | -0.464973996 | -0.561148703 | 0.028313726 | 0.246287167 | -0.435980916 | -0.366372466 | -2.715464115 | | 23 | 3.0606132 | "SID W 308924, HEMOGLOBIN EPSILON 516 | | est |
| 2636 | 0.445502162 | 0.667497933 | -0.098431163 | -0.102934845 | -0.098490089 | 0.113255903 | 0.301189085 | -2.854464564 | | 23 | 3.06062148 | "SID W 346475, ESTs [5':W79267, 3':W73953]" | | est |
| 2304 | -0.866036773 | -0.757427692 | -1.202046275 | -0.224073526 | -0.271321353 | 0.377601743 | -0.920769334 | 1.747525573 | | 23 | 3.06130441 | | 618315 | 1 |
| 1903 | -0.434186578 | -0.241240531 | -0.806135476 | -1.897064924 | -0.262544274 | -0.604771554 | 0.943298399 | 1.742468953 | | 23 | 3.06344603 | "CELL SURFACE GLYCOPROTEIN | | est |
| 594 | -0.049370788 | 0.724982888 | -0.066624582 | -1.364990234 | 0.299276114 | 1.342619658 | -1.376703739 | -0.037896372 | | 23 | 3.06369149 | | 285116 | SIOMYCIN |
| 2332 | -1.754725814 | 0.549614727 | 0.673863113 | -1.898649869 | -0.282981751 | -0.036427103 | -0.503492355 | 0.493387172 | | 23 | 3.06395533 | | 308606 | 19-Nordanosta-5 |
| 158 | -0.831058443 | -0.69707948 | -1.039282799 | -0.360333294 | -0.100151271 | 0.535327554 | -1.000055075 | 1.772130013 | | 23 | 3.06526925 | | 622282 | 4H-1-Benzothiopyran-4-one |
| 17130.1377906652.64236331 | 0.084719293 | -0.352617603 | | 0.488620314 | 0.175730467 | -0.028224427 | 0.310712874 | 233.06622008 | | | | "LYSOSOMAL PRO-X | | est |

Fig. 5C

| 501 | 502 | 503 | 504 | 505 | 506 | 507 | 508 | 509 | 511 | 510 | 518 | 519 | |
|---|---|---|---|---|---|---|---|---|---|---|---|---|---|
| 301 | -2.159048357 | -0.383745579 | -0.362219483 | -0.880174935 | -0.511359692 | -0.523803592 | -0.583517611 | -3.361118078 | 23 | 4.45166099 | | 154756 | 4(1H)-quinazolinone |
| 368 | 1.128111839 | -1.231224298 | 2.933661741 | 0.622861879 | 2.690651665 | -1.172544718 | -0.279486626 | -1.079668999 | 23 | 4.4751869 | | 319947 | 2 |
| 276 | -3.032975435 | -0.575811982 | 0.966260533 | -1.493337393 | 0.160064042 | 1.910216331 | -0.215414315 | -0.741357148 | 23 | 4.48179125 | | 671169 | 671169 |
| 130 | 0.155563205 | 0.214096382 | -2.565924644 | -1.521012902 | 1.150058309 | 0.048285119 | -2.334795952 | 0.972167492 | 23 | 4.51420643 | | 40341 | 40341 |
| 379 | 0.058175579 | 0.223759308 | 3.35061264 | -2.050938129 | 0.429938545 | -2.396489382 | -0.432906777 | -0.155698881 | 23 | 4.53169473 | | 150014 | Hydrazine |
| 867 | -0.635734499 | -0.399455513 | -0.985673428 | 0.007821307 | 0.384060115 | 1.778084159 | -0.629959522 | 3.595021248 | 23 | 4.55150948 | | 620056 | 620056 |
| 474 | 2.521326542 | -1.226664543 | 2.120594025 | -0.803828418 | -0.896755338 | -2.26730895 | 2.092172338 | -0.379149914 | 23 | 4.58190524 | | 613327 | Gemcitabine 514 |
| 840 | -1.564963735 | -1.19636045 | -1.273548663 | -0.817732751 | -0.539491653 | 1.940306425 | -1.660800722 | -1.656016734 | 23 | 4.58592133 | | 633541 | Cyclopentanone |
| 666 | 1.186946869 | -2.260094446 | 0.366966967 | -2.275680065 | -0.262134135 | -0.740920961 | 0.719174087 | -2.514783859 | 23 | 4.59505107 | | 690435 | 690435 |
| 1108 | 0.907939672 | -2.157761847 | 1.117887974 | 1.076303601 | -0.470761627 | 1.889004946 | 2.891302347 | -1.199588014 | 23 | 4.61314942 | | 133036 | SCILLIGLAUCOSIDIN |
| 1015 | -1.241233706 | 1.252034664 | -0.428988347 | 3.099374294 | 0.735473302 | -2.094081306 | 0.751816511 | -2.134509087 | 23 | 4.61880662 | | 640500 | 640500 |
| 2291 | 0.739513397 | -0.812014461 | 0.500461934 | 0.341776848 | 0.936435713 | 3.52462201 | -1.121499466 | -1.081881046 | 23 | 4.63647093 | | 632862 | Tetrakis(oxiratosilicon)(IV)tetra |
| 407 | -2.805481911 | 1.199950444 | -1.076627229 | -0.350902975 | 0.020932293 | -2.28360796 | 0.397569498 | -2.554911852 | 23 | 4.64997051 | | 687850 | 687850 |
| 149 | -1.24200666 | -1.627678156 | -1.903798819 | -1.308604002 | -0.332455873 | 1.708364001 | -1.78847332 | 0.590165496 | 23 | 4.66915155 | | 267461 | Nanaomycin |

METHODS AND SYSTEM FOR MULTI-DRUG TREATMENT DISCOVERY

FIELD OF THE INVENTION

The present invention relates to the field of disease treatment screening and disease treatment discovery, and more particularly to methods and systems for prospectively screening and finding multiple treatments that may be used more effectively than a single treatment approach to treating disease.

BACKGROUND OF THE INVENTION

The current state of drug discovery techniques largely focus on searching for a single drug which will effectively treat a disease. In the past, such techniques have been successful for diseases which are "locked in" to a single pathway for survival and/or regeneration within its host. For example, penicillin was discovered to be successful in treating many forms of bacterial diseases. However, for more complex diseases, such as the various cancers; viral diseases, such as HIV (AIDS), SARS, and others; and drug-resistant bacteria, such as tuberculosis and others, single drug treatments have not proven effective. Even for drugs which are approved as effective against such diseases, on average, such drugs will only be effective on about thirty percent of patients to which the drug is administered. Indeed, over a prolonged time scale, even penicillin-resistant bacteria have begun to emerge.

One way to explain this limited efficacy is that complex diseases may have alternate pathways along which they survive and regenerate. Those diseases which get locked into a single pathway of survival by single nucleotide polymorphism (SNP) profile can be effectively treated by a single drug that blocks the single pathway. However, some diseases, like cancer and HIV, for example, are flexible enough, so that if their primary path, as determined by the host SNP profile, is blocked using a single drug, after some time, the disease is able to change its survival path from the primary pathway to an alternate survival pathway. A multi-drug approach to these types of diseases is needed in order to block multiple survival pathways.

Although there have been some instances of multi-drug treatments of disease, such instances have been limited and disorganized, in a hindsight fashion, where there is a history of some effectiveness of two or more drugs, when each is used individually to treat a disease. The approach has then been to try the drugs together to see if an improved result can be achieved. One such example of this is the treatment of HIV by a "cocktail" approach. Another example of a multi-treatment approach, which has also been implemented only through a hindsight trial approach after experiencing some success with each treatment individually, is treatment of certain types of cancer with both radiation treatment and drug treatment. In addition to the hindsight track toward developing this regiment, it is noted that such treatments are also generally administered in sequentially, in a time-staggered fashion.

There is a need to develop organized, forward-looking ways of identifying treatment combinations for potential use together in the treatment of a disease. There is a need to treat diseases, such as viral diseases, in a complex way, because the organisms causing the diseases are very complex, able to mutate and/or use other mechanisms to survive along a different pathway when one pathway is cut off by a single treatment. Likewise, cancers, and some of the other more complex diseases that have been studied for a long time, with no cure found to date, may find more successful treatment regimens when treated multidimensionally. One-dimensional approaches (i.e., as addressed by a single type of treatment) to treatment of many of the more complex diseases have been unsuccessful to date, but generally the big pharmaceutical companies currently continue in their quests to find a "silver bullet", i.e., a single drug, to cure a disease.

What is needed are forward looking screening and discovery techniques for identifying treatments that may be used in combination for treatment of disease. Hence, treatments in combination can create the requisite complexity to challenge sophisticated diseases. There needs to be a strategy, for using foresight in developing multi-treatment approaches, and to move away from the paradigm of drug treatment, radiation treatment or other types of treatments in one-dimensional space, by thinking in multi-dimensional space, to provide treatments that act multi-dimensionally.

As noted, multiple treatments that are currently used are results of hindsight combinations. For example, it was known that the treatment of liver disease with interferon was shown to be effective, and that ribovirin could also show good results. By combining these treatments, after knowledge of their individual results, it was found that using ribovirin with interferon was more effective. Typically, drug interactions have been approached as a need to identify them to avoid them. What is needed is to look at drugs, as well as other possible types of treatment, to identify them as an advantage against disease, i.e., to identify positive interactions among multiple treatments.

SUMMARY OF THE INVENTION

The present invention provides methods, systems and recordable media for using expression data characterizing protein pathways of diseases to link relationships between treatment responses of diseased tissues to treatments applied thereto, and expression profiles of the diseased tissues as measured when untreated.

Methods, systems and recordable media are provided for screening a combination of treatments to specifically target a disease process. Differential expression levels of diseased tissues relative to at least one reference tissue are provided, either by data from previous processing of such tissues, or the tissues may be processed as part of the current procedure, using microarray technology to obtain the differential expression levels. Phenotypic/genotypic differential expression signatures or profiles are provided (either supplied as data which has already been generated, or calculated/generated from the differential expression data provided from an existing data source, or generated at the time of processing) for respective features of respective microarrays for each diseased tissue sample, relative to the at least one reference level. This gives the capability of generating a phenotypic/genotypic signature for each feature on a microarray, across the total number of diseased-tissue samples being studied.

The diseased tissues are treated with a treatment, and a treatment-response value with respect to each of the diseased tissue samples as effected by the treatment is recorded. The treatment-response vectors are used to generate a vector of phenotypic signatures representing the treatment-response vector of each of the diseased tissue samples to that treatment which was applied. Any number of treatments or treatment combinations can be successively and independently applied to treat the diseased tissues, so as to generate a vector of phenotypic signatures representing the treatment-response vector of each of the diseased tissue samples, for each treatment or combination of treatments applied.

The phenotypic/genotypic signatures of the differential expression levels and the phenotypic signatures of the treatment-response values are considered together after appropriate normalization to perform a clustering operation. Upon identifying clusters of related normalized signatures, compounds are characterized by the treatment-response phenotypic signatures caused by those treatments, and which are clustered with phenotypic/genotypic signatures representing differential expression levels representative of the diseased tissue samples. By selecting treatments linked to treatment-response signatures that are associated with different groups of genes, as identified by differential expression signatures, a multi-treatment set of treatments (which set may also include one or more individual members made up of multiple treatments, for example) can be chosen to specifically target genes involved in the disease process over a wide spectrum of protein activity. Such an approach should effectively shut off multiple pathways of survival of the disease process with minimal side effects.

Further, the present invention may be used to augment an original or existing treatment or treatment combination with a treatment or treatments that cover gene activity of a disease not addressed by the original/existing treatment or treatment combination. Still further, microarray analyses of diseased tissue samples, when dosed by the original/existing treatment may be performed to better expose disease-gene activity for which additional new treatments will be needed to impact those areas not currently impacted by the original/existing treatment.

These and other advantages and features of the invention will become apparent to those persons skilled in the art upon reading the details of the present invention as more fully described below.

BRIEF DESCRIPTION OF THE DRAWINGS

FIGS. 5A-5D show an example of a portion of a major cluster that was identified by the present method with various treatments performed on lung cancer tissues.

DETAILED DESCRIPTION OF THE INVENTION

Figure 1:
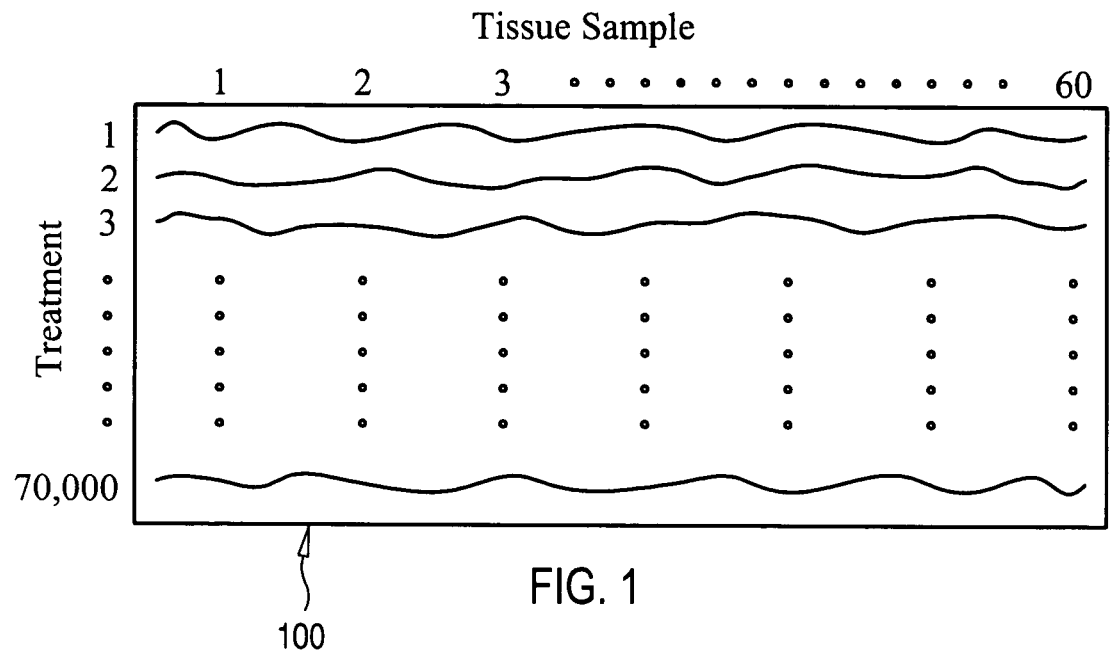
FIG. 1 shows a matrix of tissue sample responses to treatment by various treatments.

Before the present methods and systems are described, it is to be understood that this invention is not limited to particular treatments, drugs, diseases, methods, method steps, statistical methods, hardware or software described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the microarray" includes reference to one or more microarrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "genotype" refers to the actual makeup of one or more genes (DNA) in living tissue. A genotypic signature is a textual or electronic representation that directly identifies the genotype.

A "phenotype" is related to a genotype, in that it is some sort of physical expression resulting from a blueprint provided by the genotype. A phenotypic signature is a textual or electronic representation of values representing the expression that defines the phenotype. mRNA expression might be considered to be either a genotype or phenotype, as it is in a gray area where the genotype executes the phenotype. It is referred to herein as genotype/phenotype.

A "treatment" refers to the administration of an agent to living tissue (generally a diseased tissue) that has some measurable effect on protein production by that tissue, which effect can be inferred by measurement of gene expression levels of the tissue, using microarray technology. "Treatments" may refer to, but are not limited to drugs, compounds, genetic sequences used to target specific locations of the genetic makeup of the tissue, radiation, heat, cryogenics, or any other kind of application that produces an effect as described above.

A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another.

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups).

An "array" or "microarray", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. "Hybridizing" and "binding", with respect to polynucleotides, are used interchangeably. A "pulse jet" is a device which can dispense drops in the formation of an array. Pulse jets operate by delivering a pulse of pressure to liquid adjacent an outlet or orifice such that a drop will be dispensed therefrom (for example, by a piezoelectric or thermoelectric element positioned in a same chamber as the orifice). An array may be blocked into subarrays which may be hybridized as separate units or hybridized together as one array.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features), each feature typically being of a homogeneous composition within the feature. Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample (for example, a fluorescently labeled polynucleotide or protein containing sample) and the array then read. Reading of the array may be accomplished by illuminating the array and reading the location and intensity of resulting fluorescence at multiple regions on each feature of the array. For example, a scanner may be used for this purpose which is similar to the AGILENT MICROARRAY SCANNER manufactured by Agilent Technologies, Palo Alto, Calif. Other suitable apparatus and methods are described in U.S. patent applications: Ser. No. 10/087,447 "Reading Dry Chemical Arrays Through The Substrate" by Corson et al.; and in U.S. Pat. Nos. 6,518,556; 6,486,457; 6,406,849; 6,371,370; 6,355,921; 6,320,196; 6,251,685; and 6,222,664. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,251,685, U.S. Pat. No. 6,221,583 and elsewhere). A result obtained from the reading may be used in accordance with the techniques of the present invention in screening and finding multiple drug treatment therapies. A result of the reading (whether further processed or not) may be forwarded (such as by communication) to a remote location if desired, and received there for further use (such as further processing).

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

FIG. 1 shows a matrix 100 wherein each column represents one of sixty samples (i.e., cancer cell lines) from the National Cancer Institute that were tested for responses to various drugs, with each of the rows representing a drug that was used to treat the tissues. There are currently about 70,000 drugs to be tested individually against the sixty samples, but not all are shown in the figures, for the purpose of simplifying the explanation. Optionally, one could test specific combinations of compounds on the cell lines. Further, as noted above, other types of treatments (e.g., radiation at various levels, other compounds, genetic sequences, and/or the like) could be applied and tested in addition to the drugs shown, or alternatively to this test Also in this specific application, only one response to an application of a combination of treatments/compounds is measured. Thus, row 1 shows the phenotypic signature of the response of the sixty tissues to treatment/drug 1. The phenotypic signature includes a treatment (in this case, drug) response value related to expressed levels of proteins used by the disease, e.g., concentration of drug (or level o radiation, or amount or dose of some other treatment) required to inhibit tumor growth by fifty percent over a specified time interval, referred to as $GI_{50}$, for each of the sixty cells (tissue samples) to which the treatment/drug was applied. Different techniques may be used for the treatment and response measurement. One approach is to determine how much of the treatment needs to be applied to retard cell growth by fifty percent over a fixed amount of time ($GI_{50}$). Another approach is to apply a fixed amount of the treatment/drug and see how much inhibition results over a fixed amount of time.

The phenotypic response gives a signature of the variation in the response to the treatment/drug as it impacts disease-active proteins, the levels of which vary across the samples. The mRNA transcription sequences (from the genes, which range up to about 30,000) may number from about 100,000 to 200,000 varieties as produced by gene mutations, varying transcription factors, and/or splice variants and other factors modifying the basic gene message. The phenotypic signatures across the sixty samples are thus induced by level variations of disease-specific proteins as produced by a subset of the 100,000 to 200,000 possible transcription signatures as modified by translation factors specific to each of the sixty cell-line samples. Such response profiles are measured for each of about 70,000 candidate treatments. Each treatment-free mRNA signature is ratioed to its corresponding baseline reference signature to produce a differential-expression profile to characterize disease activity. Thus, after appropriate transformation and normalization, each treatment-induced phenotypic signature in FIG. 1 are compared with differential-expression signatures from genes measured on a single two-color microarray or two single-color microarrays, to map compounds to the transcriptome locations of the diseased tissue samples. Additionally, replicates may be run of each tissue sample against each treatment, to perform an average response with regard to each, to reduce the noise in the phenotypic signatures. Likewise, replicate arrays may be run to reduce noise in gene expression readings. Additionally or alternatively, phenotypic signatures may be processed using "self-self" prediction techniques such as described in co-pending, commonly owned application Ser. No. 10/400,372 filed Mar. 27, 2003 and titled "Method and System for Predicting Multi-Variable Outcomes", and in Application Ser. No. 60/368,586 filed Mar. 29, 2002 and titled "Generalized Similarity Least Squares Predictor", both of which are incorporated, in their entireties, by reference thereto.

Figure 2:
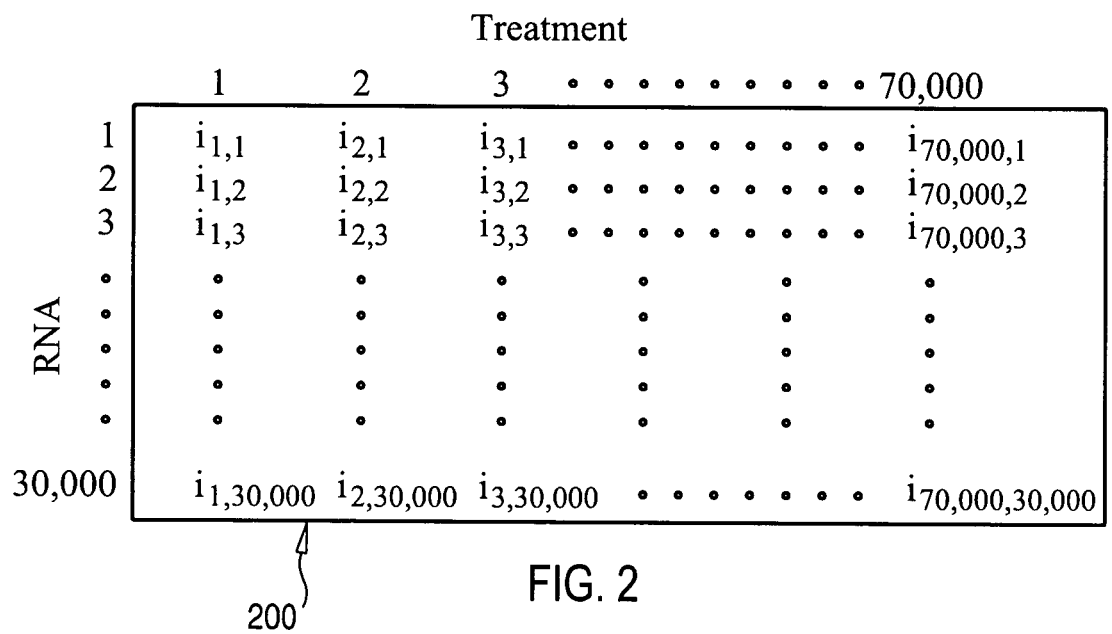
FIG. 2 show a correlation matrix generated using the treatment profiles in response to the various treatments as shown in FIG. 1 and mRNA expression profiles from microarray experiments on the diseased tissue samples of FIG. 1. Optionally, the set of tissue samples may or may not be biologically conditioned and/or under treatment according to a specified protocol and/or treatment regimen.

Thus, in FIG. 1, each of the tissues is run once treatment-free on a microarray analysis, to create a basis for screening all treatments. For example, there may be 30,000 features on a microarray used to run the analysis. This produces 30,000 signatures, across the sixty sample tissues, to be compared with each overall treatment-induced phenotypic signature shown in FIG. 1. A typical approach to try and find relationships among data on this order of magnitude would be to produce a correlation matrix 200 on the order of about 70,000×30,000 values. For example, the 70,000 treatments are identified over the columns of the matrix 200 shown in FIG. 2, with 30,000 mRNA values identified in the rows of the matrix 200. Such a correlation matrix 200 is generated by calculating the inner product of the values of the 70,000 treatment phenotypes (see FIG. 1) with the 30,000 mRNA signatures and typically centered by means and scaled by standard deviation. The inner product may be calculated as follows:

$$\frac{\overline{D_j} \cdot \overline{mRNA_k}}{N} = i_{j,k}$$

where $\overline{D_j}$ is the vector representing the phenotypic expression across samples when treated with the $j^{th}$ treatment in the list, where j ranges from 1 to 70,000 treatments, in this example;

$\overline{mRNA_k}$ is the vector representing the sample profile of differential-expression for the $k^{th}$ mRNA sequence (gene), as measured from microarray analysis(es), where k ranges from 1 to 30,000, in this example;

N is the number of samples, e.g., 60 cell lines; and $i_{j,k}$ is the value in correlation matrix 200 filling the $j^{th}$ column and the $k^{th}$ row.

Thus, the values in matrix 200 are a cross product of normalized or standardized vectors, and optionally centering by subtracting a vector mean value. Once matrix 200 is produced, then various clustering techniques may be applied to try and identify blocking patterns in the data, or "clusters" which might indicate that certain treatments are effecting certain groups of mRNA. Alternatively, clustering techniques may be applied to the treatment and mRNA matrices prior to performing the cross product operation, in an effort to reduce the sizes to something less than 70,000 and 30,000 vectors, respectively.

The present inventor believes that important information is dropped or lost when such data is processed into a correlation matrix, such as by performing a cross product/inner product procedure to obtain matrix 200, as described above. When such an operation is performed, phase information is lost, as is well-known, particularly among electrical engineers. Because the phenotypic responses to the treatments at issue are measured as the output (i.e., phenotypic signature) and the inputs are the mRNA values, there is a protein link between the input and output, i.e., the mRNA instructs the generation of proteins in response to the disease. Treatments impact disease proteins to produce the phenotypic output response. Thus, the present inventor believes that it is important to consider the phase relationships between the inputs (mRNA) and outputs (phenotypic responses), as important factors based on the protein links between the inputs and outputs.

Figure 3:
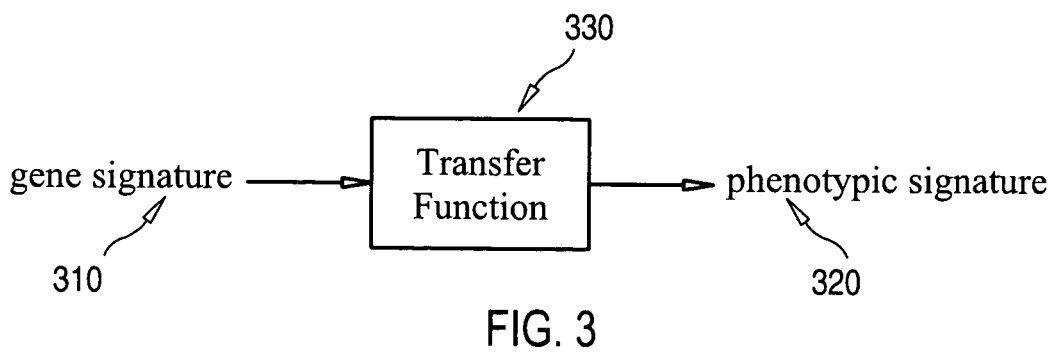
FIG. 3 schematically illustrates a "black box" model which relates the genotypic signature of a treatment response to the phenotypic signature via a transfer function. More generally, the black box may represent a multiple-input/multiple-output (MIMO) transfer function involving groups of genes and multiple reactions to treatment(s) dosage.

Hence, the approach taken by the present invention is akin to a lumped parameters modeling approach. Referring to FIG. 3, the genotypic signature of mRNA is modeled as the input 310, the phenotypic signature is modeled as the output 320, and a "black box" 330 represents a transfer function that transforms input 310 to output 320. Note that input 310 and output 320 may be single inputs and outputs, e.g., a single gene and single drug impact or single protein production, or multiple inputs and outputs, e.g., groups of genes producing groups of proteins and/or multiple drug impacts. The present invention is adapted to further modifications within the black box as additional information becomes known about the relationships between genes and the production of proteins resultant therefrom. This will enable the input and output to be modeled, for example, like an electrical circuit, with black box 330 containing "resistances", "inductances", "capacitances", "emfs", etc., that model the best knowledge that is gained with regard to the relationships between the genes and proteins produced therefrom, which will enable the modeling of an accurate phase relationship between the mRNA signatures and the phenotypic signatures. Such complete modeling knowledge is currently not known however, and it may be at least five years, or more, before such knowledge is obtained in sufficient detail.

Figures 4, 6:
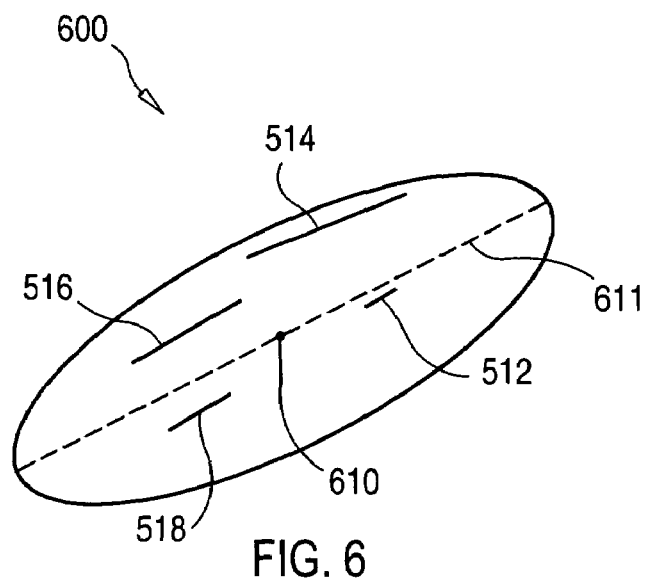
FIG. 4 shows a matrix which includes genotypic/phenotypic gene signatures along with phenotypic signatures in response to treatments administered to tissue samples.
FIG. 6 is a schematic representation of an ellipsoid which represents the plot of a cluster of vectors from a matrix such as the matrix shown in FIG. 4, or the matrix from which the data generated in FIG. 5 was based on. As noted, this is a schematic representation, as, in reality, data ellipsoids are hyperdimensional with complicated radial and angular geometries.

In the meantime, this technique assumes that an input signature is either in phase (0°), or out of phase (i.e., 180° out of phase) with the output signature. This assumes that a gene is either directly related to (i.e., involved in the production of) a protein that is expressed (in sync, or in phase) or involved in regulating the production of the protein (trying to counteract the expression of the protein, i.e., perfectly out of sync or out of phase). Therefore an "out of phase" signature is generated in addition to the "in phase" signature which is read from the microarray results. Rather than taking a cross product and forming a correlation matrix, this methodology assembles all of the signatures, after appropriate transformation such as by use of Log transforms, into one large list of profiles, properly normalized, as shown in FIG. 4.

Matrix 400, for the example that we have been discussing, includes sixty columns, one for each tissue sample. The rows of matrix 400 include the mRNA signatures (which may be thought of as genotypic profiles or phenotypic profiles (genotypic/phenotypic profiles)), which in this example includes 60,000 rows (although it could range up to about 400,000 rows, if functional variants are considered separately) since the signatures are represented as "in phase" and "out of phase", and thus result in two signatures for each of the 30,000 features on the microarray. The "out of phase" signatures are generated by inverting the "in phase" signatures that are read from the microarray. Matrix 400 further includes the phenotypic signatures, which are the responses to the treatments (in this example, 70,000 rows).

Rather than clustering within a single zone (i.e., the zone containing the 60,000 genotypic/phenotypic mRNA-expression signatures or the zone containing the 70,000 phenotypic drug-induced signatures), or performing a cross product correlation to combine these two zones (thereby losing valuable information, as discussed above), clustering procedures are performed over the entire matrix 400 as a whole. Each of the signatures are normalized for comparison purposes. One method of normalizing used is by Z-scoring, although other normalization methods may be substituted. Also weighting techniques may be applied so that highly upregulated features do not receive overamplified attention during the clustering process. Further, noisy profiles may be weighted with relatively reduced weight.

Clustering of the information is performed using any cluster technique that is capable of clustering similar signatures, such as K-means or other known techniques. However, it is preferred to perform the clustering using the tools and techniques described in co-pending, commonly owned application Ser. No. 09/986,746 filed Nov. 9, 2001 and titled "System and Method for Dynamic Data Clustering" which application is incorporated herein, in its entirety, by reference thereto. Similarity may be defined by the Euclidean distance between the normalized vectors in matrix 400. These dynamic clustering techniques are scalable, and paralellizable, so that they can handle large scale problems such as those presented in the context of the present invention. The result of these clustering operations gives clusters which contain mixtures of phenotypic signatures (treatment signatures from the 70,000 row zone) and genotypic/phenotypic signatures (expressed disease gene (mRNA) signatures from the 60,000 row zone). Sometimes the clustering occurs among genes in phase and sometimes with genes out of phase. Some cluster may contain only treatment-induced signatures and some clusters may contain only mRNA-expression signatures. The clusters of interest to the present techniques contain both types of signatures.

FIGS. 5A-5D show an example of a portion of a major cluster that was identified by the present method with various treatments performed on lung cancer tissues. The method employed measures the distance that each profile is from the densest part of a high dimensional ellipsoid characterizing the cluster that the profiles are identified as belonging to. The distances are identified under the "DISTANCE" column 510 in the chart shown in FIGS. 5A-5D.

FIG. 6 is a schematic representation of an ellipsoid 600 which represents the plot of a cluster of vectors from a matrix such as matrix 400 or a similar matrix assembled (such as that for the example of FIG. 5), when the vectors are plotted in high dimensional space. The clustering techniques described above are designed to find and identify such clusters, as well as locate the densest part of each ellipsoid cluster, shown as diagonal or "ridge" 610 in FIG. 6. Using a dynamic data clustering system as disclosed in application Ser. No. 09/986,746, the system uses force functions to converge a mathematical probe to the densest part of a profile cluster. Thus, the system not only identifies the clusters but defines a point of reference for all profiles in the cluster, with respect to each cluster identified. The distance of each profile from the center of the cluster it belongs to can be defined by any viable distance metric. An example of a distance metric used is Euclidean distance. The relative angular positions of the profiles may also be consequential for selecting combinations of effective treatments.

The distance values from the center are identified as "DISTANCE" for the calculations made with regard to the data in the example shown in FIGS. 5A-5D. "Sevinon" is noted as being a member of a group of similar treatments that are the closest to the densest location 610 of the ellipsoid in the example of FIG. 5A, as noted by the subgroup 530. FIGS. 5A-5D show a portion of the clustering results for a subset of the sixty cell lines discussed above, where the subset were tissue samples that are specific to lung cancer. FIGS. 5A-5D show data from only a portion of the most dominant cluster identified by the process (cluster 23). Column 501 (Idrow) identifies the row index of each profile shown in the data. Columns 502-509 contain values that make up the profiles that were identified in the cluster. Column 511 identifies the cluster to which the displayed profiles were found to belong (in this case, cluster 23). Column 510 indicates "DISTANCE", which is a distance measurement from the densest location 610 in the cluster. Columns 518 and 519 contain treatment identifiers (in this example, drug identifiers) and gene identifiers by name and by NSC identifier (as provided by NIH).

It can be observed that the data (arranged in rows which characterize profiles, which can be expressed as vectors, plotted on an ellipsoid, as discussed) is arranged in four subgroups in this example, with the first subgroup 530 being those results which are the closest to the densest location 610 of the ellipsoid, subgroup 540 being the next closet subgroup, subgroup 550 being further away from the densest location 610 than subgroup 540, but closer than subgroup 560, and subgroup 560 being the furthest from the densest location 610, out near the periphery of the ellipsoid 600.

Although the distances measured do not identify angularity between profiles, or which side of the ridge 611 (dominant, principal axis running through the densest location) a particular vector (profile) lies on, the distance value does give an indication of how close to the ridge 611 and densest location 610 that vector lies. For example, the distance 512 for "Sevinon", which is located in subgroup 530, is shown close to ridge 610 in FIG. 6. Another treatment vector for "Gemcitabine", located in subgroup 560, was measured 514 to be further from ridge 611 as shown in FIG. 6. A third treatment vector for "Paclitaxel-Taxol" located in the subgroup 550, is shown at a somewhat intermediate distance 516 relative to distances 512 and 514, and the treatment vector for "Mitoxantrone", located in subgroup 540, is shown at an intermediate distance 518 between the distances for 512 and 514.

The present approach is to find a combination of treatments, such as those represented in FIG. 6, that show relationships to different genes in the clustered profile, so that each treatment appears to be related to different combinations of genes involved in the disease process. The treatments are then combined and tested together, each in a low dose/amount to observe whether a combinatorial synergistic effect on this disease is achieved by the combination. Serendipitously, the low dose/amount combination reduces the side effects of each individual treatment in the combination. Of course any combination where an adverse reaction occurs among two or more treatments in the combination used would be discarded as being unsuitable for use as a potential treatment combination. Useful combinations will specifically and effectively target the disease process being studied.

Further, by identifying the treatment vectors as in the example shown above, various combinations of treatments in a treatment family (such as, for example, drugs in the drug family, or related compounds in a compound family) of each identified treatment vector may be tested in the manner described above, as related treatments in a treatment family (e.g., drugs in a drug family) will generally fall within similar relative distances from the densest location of the ellipsoid. For example each of the following family members of the Sevinon family may be substituted for Sevinon, that was originally tested in the selected combination of drugs: Declid; Desenex, solution; a component of Desenex; Renselin, Undec-10-enoic acid; Undecyl-10-enic acid; Undecylenic acid; UNDECEN-10-ACID-1; WLN:QV9U1; 10-Hendecenoic; 10-Henedecenoic acid; 10-Henedecenoic acid; 10-Undecenoic acid (8CI9CI); 10-Undecylenic acid; and 9-Undecylenic acid.

In this way, the combinations of treatments may be predicted to try as potential combinations for multiple treatments in patients which will address the broadest spectrum of genes related to the production of proteins seen as elevated or inhibited when a tissue is in the disease state. By testing the predicted combinations, useful combinations for treatment in patients will be much easier to identify. The present invention is a forward—looking way of choosing and predicting specific combinations of treatments to test, e.g., using high-throughput (HTP) screening of treatment combinations, and as such, greatly reduces the time to finding successful combinations, which currently have only been discovered accidentally, through hindsight and experiences gained through individual treatments.

The treatments identified are targeted to the genes involved in the disease process. Because of this, the chances of significant side effects are reduced. For those combinations found to be effective in the sample tissues, further testing, such as animal testing would be warranted to study any effects the treatments may have on normal tissues within an organism, since the testing with the disease tissue samples only proves that the combination of drugs applied is effective at treating the diseased tissues. For the cancer examples discussed above, testing with the tissue samples would only show that the combination of treatments effectively kills the cancer cells, or not. Animal testing would further show the effects of the treatment combination on the normal tissues in the organism, to see if the animal survives the treatment combination.

Protein pathways, implicated by differential gene expression levels when comparing treated tissues to non-treated tissue and among diseased and non-diseased tissues are used to produce phase relations between treatment responses and expression profiles across the tissue samples being tested. An example of such is the sixty cancer cell lines referred to above. Using the techniques described above, all phase-related profiles are normalized and clustered. The number and sizes of the resulting clusters may indicate their relative importance as to effective treatments. For example, cluster 23, a portion of which is shown in FIGS. 5A-5D was very large and very dominant with respect to other clusters identified. The structure of each cluster infers treatment-gene associations to guide multi-treatment selections.

Figure 7:
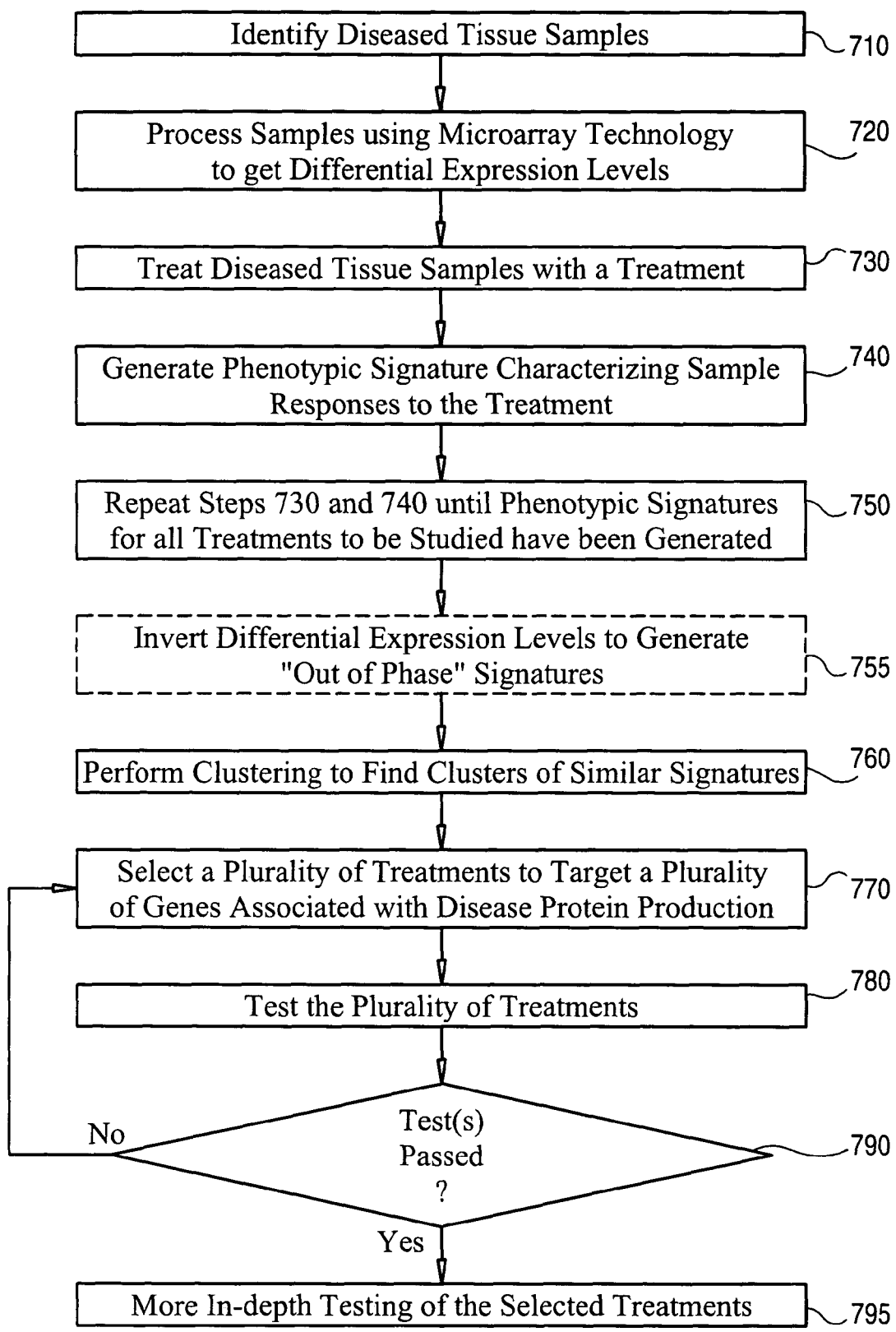
FIG. 7 is a schematic flowchart exemplifying steps that may be performed in carrying out a multi-treatment screening method according to one embodiment of the present invention.

FIG. 7 is a schematic flowchart exemplifying steps that may be performed in carrying out a multi-treatment discovery method according to one example of the present invention. At step 710, diseased tissue samples are procured and identified. These samples are for testing treatment hypotheses against. For example, one method performed used sixty cancer cells lines received from the National Cancer Institute. The samples may be next processed (step 720) using microarray technology, without any treatments being applied to get baseline disease phenotypic signatures of proteins expressed by the diseased tissues. Alternatively, processing may begin with baseline disease phenotypic signatures having been already determined and supplied from another source, such as an outside supplier or research facility, for example. The tissue samples may be human or animal. The diseased tissues are run against a reference, such as healthy tissue(s) of the same type, or a pooled reference of normal tissues, or some other established normal sample that establishes a normal baseline of protein productions, using a two-color, two channel array, or by comparing signals from two single-channel arrays. This comparison process determines the excess amounts or protein and/or inhibited amounts of protein being produced in each of the diseased tissues, relative to normal production. These differential expression readings are what are plotted to produce the diseased tissue baseline phenotypic/genotypic signature across the total number of tissue samples. It is also noted that, alternatively, these differential expression reading may be supplied from an already existing source, such as a database containing results from processing already having been previously accomplished.

Hence, the comparison of the baseline phenotypic signatures of the diseased tissues with baseline phenotypic signatures of normal or reference tissues gives expression ratios of the proteins, absent any impaction by treatments. The expression ratios indicate protein levels that treatments must impact/compensate in order to be effective against the disease. Thus, for each gene, the phenotypic signature of expression for that gene across all of the diseased tissues is determined by microarray processing. That phenotypic signature is compared to a reference of some sort, such as a phenotypic/genotypic signature of a healthy cell sample, or a pooled reference containing an average phenotypic signature of several healthy cell samples, for example. This comparison gives an idea of how much the diseased genes are upregulated or downregulated, in the diseased tissues, without any treatment, i.e., the ambient activity of the disease, with respect to each gene observed.

Next, the diseased tissue samples are treated with a treatment (e.g., compound, drug, radiation, genetic sequence, or other type of treatment) at step 730, and responses to the treatment are measured with respect to each tissue sample. A phenotypic signature is generated from the measured responses to the treatment at step 740. Typically, a measurement is taken as to what concentration/amount of the treatment is required to reduce the tissue growth by fifty percent over a fixed period of time, or a measurement of how much the tissue growth slows over a fixed period of time given a fixed amount (concentration) is measured. Note, however, that these are only example measurements, and that any measurement that quantitatively relates the impact on the disease-related proteins with the treatment being administered can be used to generate the phenotypic signatures. In the first example given, the concentration values are recorded with regard to each diseased tissue, and these values make up the phenotypic signature for the treatment having been administered. Tissue growth may be measured by volumetrically, by area of a sample, diameter of a sample, mass of a sample, or other quantitative comparison measurement technique, for example.

In reducing the tissue growth, it is inferred that the treatment blocks or inhibits expression of some of the proteins expressed by the genes. The amount of treatment that it takes to block or inhibit such expression depends upon the amount of protein that was expressed in each sample when no compound was applied. Therefore, a variation in treatment response across the diseased-tissue samples results because there is a variation in the amount of protein produced in each sample as a response to the disease. The proteins are produced from the gene expression message (mRNA that was measured). By comparing the treatment-phenotypic signature with the baseline diseased tissue expression ratios, a treatment-phenotypic signature which is similar to a phenotypic signature produced by a particular mRNA infers that the treatment that was administered has an impact on a protein produced as a result of the expression of that gene/mRNA. Also, "out of sync" or "out of phase" diseased/baseline signatures which are similar to a treatment-phenotypic signature may infer an effect of that particular treatment on the particular gene/mRNA characterized by the "out of sync" or "out of phase" signature, as a gene may play some role in the production of the protein through direct or indirect inhibition.

Steps 730 and 740 are repeated to generate phenotypic signatures with regard to each treatment to be tested against the diseased tissue samples. It is noted that each treatment applied during this process need not be of the same type. For example, a radiation treatment may be the next treatment to be processed, followed by an additional drug treatment. Any possible combination of treatment signatures may be generated for screening as described. Further optionally, "out of sync" or "out of phase" phenotypic signatures for the differential expression levels of the ambient state of the diseased tissue may be generated at step 755, for use in comparison as described above, by inverting the signature values measured in step 720. In either case, all phenotypic signatures are considered together, as described above. At step 760, clustering of the signatures is performed (typically after normalizing the profiles (signatures).

Analysis of a cluster of profiles is performed to determine candidate treatments that are clustered with particular mRNA(gene) profiles. By selecting a plurality of treatments at step 770, each of which is shown to be similar to a different gene or group of genes (as shown by its plot in the cluster ellipsoid, as well as similarity measurements with respect to ambient diseased tissue phenotypic profiles), and each of which also belongs to the same cluster, a prediction for a multi-treatment of the disease against which the treatments were tested may be made. A goal of this type of selection for a predicted multi-treatment regimen, is to treat, by directly targeting as many genes as possible that are linked to the production of proteins involved in the growth of the disease tissue. By using this broad-spectrum approach, while at the same time specifically targeting the genes populating the broad spectrum, significantly smaller doses/amounts of each treatment may show combinatorial efficacy, and all pathways along which the disease can survive may be cut off.

After a candidate group of treatments has been selected at step 770, the plurality of treatments are tested at step 780, initially to rule out a combination if it clearly lacks efficacy, or is unacceptably toxic, for example. One method of testing the plurality of treatments as a combination treatment for an initial reading of efficacy, is to treat the diseased tissue samples with the selected treatment combination and monitor, as described above, to determine what degree, if any, of inhibition of the disease the treatment combination causes. If the degree of inhibition is less than a predetermined amount, then the selected group of treatments fails this test at step 790. Otherwise, it passes, and the selection of treatments may be continued to use for further, more in-depth studies (step 795), such as animal studies, for example.

Another type of testing that may be performed at step 780 in addition, or alternative to that previously mentioned, is to determine an ADME (Adsorption, Distribution, Metabolism, and Elimination) profile of the combination of treatments or an ADME-tox (Adsorption, Distribution, Metabolism, Elimination and Toxicity) profile. This can be performed by comparing the expression profiles of tissues treated with the selected treatment combination, with gene-expression profiles characterizing the results of treatment of similar tissues with one or more treatments having known toxic characteristics which are unacceptable for use in treatment. By performing similarity comparisons, if the expression results from treatment with the selected treatment combination are closer than a predetermined threshold to expression results from treatment with any known treatment that has unacceptable toxicity, then the selected group of treatments fails this test at step 790. Otherwise, it passes, and the selection of treatments may be continued to use for further, more in-depth studies (step 795), such as animal studies, for example.

When a selected group of treatments fails testing at step 790, processing returns to step 770, where another plurality of treatments is chosen, which is different from any previously selected combination, although selected by the same selection criteria.

Hence, efficacy and toxicological-pharmacological properties of individual treatments and selected treatment combinations may be predicted by estimation or measurement of their impact on all genes to produce an expression signature for comparison with gene expression profiles of known efficacy and ADME-tox properties using the herein described methodology.

An optional technique may be employed while processing according to the techniques described in FIG. 7, to prospectively eliminate, or predict certain treatment combinations likely to prove ineffective or toxic. This technique involves, in addition to those steps described in FIG. 7, generating phenotypic signatures characterizing sample responses to treatments (each preferably individually applied to the samples, like in step 740) having known, unacceptable toxicity characteristics, known ADME-tox profiles which are undesirable, and/or are known to lack efficacy. These profiles/signatures are added to the matrix containing the treatment-induced profiles being tested, as well as the in-phase and out-of phase signatures characterizing the tissue samples when they are not being treated with a treatment. Then, when clustering is performed at step 760, the known signatures are noted as to their relative positions in the resulting clusters. Treatment-induced signatures located at a distance (such as Euclidean distance, for example) from a signature characterizing an undesirable known treatment that is less than a predetermined distance, are considered to be too similar to the undesirable treatment, and are not selected at step 770, but automatically eliminated from further processing. This decreases the time to process such a large number of treatments in the quest to find acceptable treatment combinations.

Embodiments of the present invention as described herein employ various process steps involving data stored in or transferred through computer systems. The manipulations performed in implementing this invention are often referred to in terms such as calculating, normalizing, or solving. Any such terms describing the operation of this invention are machine operations. Useful machines for performing the operations of embodiments of the present invention include general or special purpose digital computers, analog computational devices/computers or other similar devices. In all cases, there is a distinction between the method of operations in operating a computer and the method of computation itself. Embodiments of the present invention relate to method steps for operating a computer in processing electrical or other physical signals to generate other desired physical signals.

Embodiments of the present invention also relate to an apparatus for performing these operations. This apparatus may be specially constructed for the required purposes, or it may be a general purpose computer selectively activated or reconfigured by a computer program and/or data structure stored in the computer. The processes presented herein are not inherently related to any particular computer or other apparatus. In particular, various general purpose machines may be used with programs written in accordance with the teachings herein, or it may be more convenient to construct a more specialized apparatus to perform the required method steps.

Figure 8:
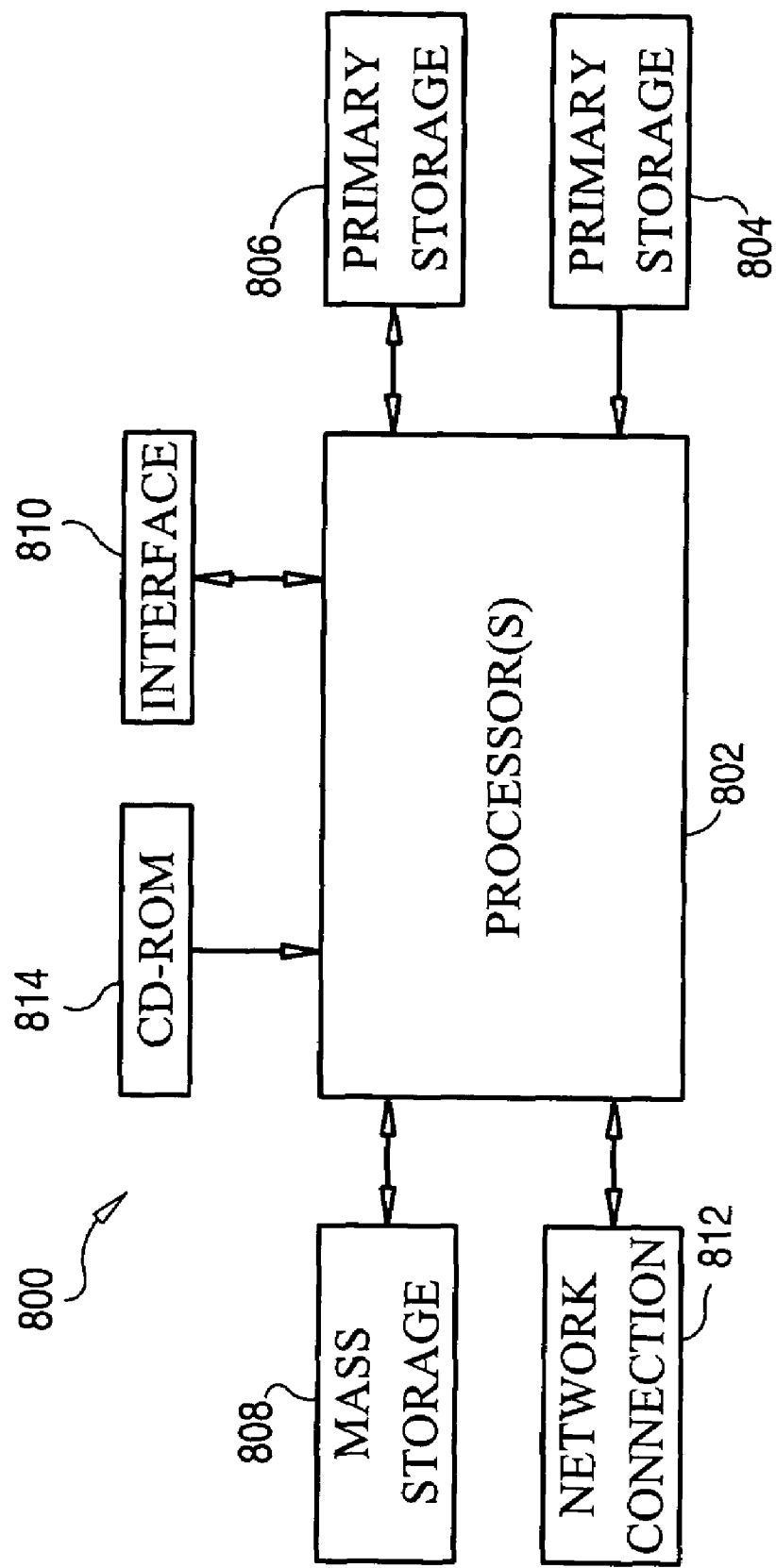
FIG. 8 is a block diagram illustrating an example of a generic computer system which may be used in implementing the present invention.

FIG. 8 illustrates a typical computer system in accordance with an embodiment of the present invention. The computer system 800 includes any number of processors 802 (also referred to as central processing units, or CPUs) that are coupled to storage devices including primary storage 806 (typically a random access memory, or RAM), primary storage 804 (typically a read only memory, or ROM). As is well known in the art, primary storage 804 acts to transfer data and instructions uni-directionally to the CPU and primary storage 806 is used typically to transfer data and instructions in a bi-directional manner Both of these primary storage devices may include any suitable computer-readable media such as those described above. A mass storage device 808 is also coupled bi-directionally to CPU 802 and provides additional data storage capacity and may include any of the computer-readable media described above. Mass storage device 808 may be used to store programs, data and the like and is typically a secondary storage medium such as a hard disk that is slower than primary storage. It will be appreciated that the information retained within the mass storage device 808, may, in appropriate cases, be incorporated in standard fashion as part of primary storage 806 as virtual memory. A specific mass storage device such as a CD-ROM 814 may also pass data uni-directionally to the CPU.

CPU 802 is also coupled to an interface 810 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 802 optionally may be coupled to a computer or telecommunications network using a network connection as shown generally at 812. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for clustering vectors may be stored on mass storage device 808 or 814 and executed on CPU 808 in conjunction with primary memory 806.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, treatment, tissue sample, process, process step or steps, to the objective, spirit and scope of the present invention. All such modifications are intended to be within the scope of the claims appended hereto.

That which is claimed is:

1. A method for screening a combination of treatments to specifically target a disease process, wherein the disease process impacts gene expression, said method comprising the steps of:
    (a) providing differential expression levels of predetermined genes of diseased tissue samples relative to at least one reference tissue for respective features of microarrays targeting the predetermined genes, wherein each feature targets a specific gene, said features being used to calculate the differential expression levels;
    (b) for each of the respective features of respective microarrays for each diseased tissue sample, providing a single phenotypic/genotypic signature representing the differential expression level for each diseased tissue sample for that feature across the respective microarrays;
    (c) treating the diseased tissue samples with a treatment;
    (d) measuring a treatment-response value with respect to each of the diseased tissue samples as effected by the treatment;
    (e) generating a single phenotypic signature representing the treatment-response values of each of the diseased tissue samples;
    (f) repeating steps (c)-(e) with a different treatment at least once so that multiple phenotypic signatures have been generated for multiple treatments;
    (g) performing a clustering operation based on the phenotypic/genotypic signatures of the differential expression levels and the phenotypic signatures of the treatment-response values together; and
    (h) selecting treatments by identifying the treatment-response phenotypic/genotypic signatures caused by those treatments, and which are clustered with phenotypic signatures representing differential expression levels representative of the diseased tissue samples.

2. The method of claim 1, wherein said providing differential expression levels further comprises processing the diseased tissue samples and the at least one reference tissue using microarray technology to obtain the differential expression levels of the diseased tissues relative to the at least one reference tissue.

3. The method of claim 2, wherein said processing to obtain differential expression levels comprises processing a diseased-tissue sample and the reference tissue on a two-color, two channel microarray apparatus.

4. The method of claim 2, wherein said processing to obtain differential expression levels comprises processing a diseased-tissue sample on a single channel microarray apparatus, processing the reference tissue on a single channel microarray apparatus, and comparing the results of the processing.

5. The method of claim 1, wherein said providing a phenotypic/genotypic signature representing the differential expression level for each tissue sample for that feature, respectively, comprises generating the phenotypic/genotypic signatures based on the differential expression levels provided.

6. The method of claim 1, wherein each said treatment is selected from the group consisting of: a drug, a combination of drugs, a compound, a combination of compounds, radiation, a genetic sequence, a combination of genetic sequences, heat, cryogenics and a combination of two or more of any of the previous members in this group.

7. The method of claim 1, further comprising the steps of:
labeling the phenotypic/genotypic signatures representing the differential expression levels as "in phase" signatures;
generating "out of phase" signatures by inverting the "in phase" signatures; and
including the "out of phase" signatures with the "in phase" signatures and the treatment-response signatures when performing steps (g) and (h).

8. The method of claim 7, wherein said phenotypic signatures are normalized prior to said clustering.

9. The method of claim 1, wherein said clustering operation includes finding a density center of a cluster, and calculating distances of the phenotypic signatures, belonging to the cluster, from the density center.

10. The method of claim 9, wherein the selection of treatments is made to address a broad spectrum of genes involved in the disease process of the diseased tissues.

11. The method of claim 9, wherein the treatments are selected by selecting treatment-response signatures within a cluster and having varying distances from the density center.

12. The method of claim 1, wherein said phenotypic signatures are normalized prior to said clustering.

13. A method comprising forwarding a result obtained from the method of claim 1 to a remote location.

14. A method comprising transmitting data representing a result obtained from the method of claim 1 to a remote location.

15. A method comprising receiving a result obtained from a method of claim 1 from a remote location.

16. The method of claim 1, wherein each treatment-response value comprises a concentration level or amount of the treatment used to block or retard the growth of the tissue by a predetermined percentage over a predetermined period of time after treatment.

17. The method of claim 1, wherein each treatment-response value comprises a value characterizing the amount of blocking or retardation of growth of the tissue over a predetermined period of time after treatment with a fixed amount of the treatment.

18. The method of claim 1, further comprising generating at least one phenotypic signature representing treatment-response values of each of the diseased tissue samples resultant from treating the diseased tissue samples with at least one treatment having known undesirable characteristics for treatment of the diseased tissues;
including that at least one phenotypic signature resulting from said treatment having known undesirable characteristics with all other signatures included in performing the clustering step (g); and
discarding any phenotypic signature representing treatment-response values from candidacy for the selection step (h) when the phenotypic signature is less than or equal to a predefined distance from a location of the at least one phenotypic signature resulting from treatment with a treatment having known undesirable characteristics.

19. The method of claim 18, wherein said known undesirable characteristics comprise an unacceptable level of toxicity.

20. The method of claim 18, wherein said known undesirable characteristics comprise an insufficient efficacy.

21. A method of augmenting an original or existing single treatment or treatment combination for a disease with at least one additional treatment that covers gene activity of the disease not addressed by the original or existing treatment, said method comprising the steps of:
(a) providing differential expression levels of predetermined genes of diseased tissue samples relative to at least one reference tissue for respective features of microarrays targeting the predetermined genes, wherein each feature targets a specific gene, said features being used to calculate the differential expression levels;
(b) for each of the respective features of respective microarrays for each diseased tissue sample, providing a phenotypic/genotypic signature representing the differential expression level for each diseased tissue sample for that feature across the respective microarrays;
(c) treating the diseased tissue samples with the original or existing single treatment or combination treatment;
(d) measuring a treatment-response value with respect to each of the diseased tissue samples as effected by the original or existing single or combination treatment;
(e) generating a phenotypic signature representing the treatment-response values of each of the diseased tissue samples as effected by the original or existing single or combination treatment;
(f) treating the diseased tissue samples with a treatment that is not included in the original or existing single or combination treatment;
(g) measuring a treatment-response value with respect to each of the diseased tissue samples as effected by the treatment that is not included in the original or existing single or combination treatment;
(h) generating a phenotypic signature representing the treatment-response values of each of the diseased tissue samples as effected by the treatment that is not included in the original or existing single or combination treatment;
(i) repeating steps (f)-(h) with a different treatment that is also not included in the original or existing single or combination treatment at least once so that multiple phenotypic signatures have been generated for multiple treatments not included in the original or existing single or combination treatment;
(j) performing a clustering operation based on the phenotypic/genotypic signatures of the differential expression levels and the phenotypic signatures of the treatment-response values together; and
(k) selecting at least one treatment by identifying the treatment-response phenotypic signatures caused by the at least one treatment, and which are clustered with phenotypic signatures identifying the treatment-response phenotypic signatures caused by the treatment or treatments in the original treatment, as well as with phenotypic/genotypic signatures representing differential expression levels representative of the diseased tissue samples, but separated from the phenotypic signatures identifying the treatment-response phenotypic signatures caused by the treatment or treatments in the original treatment, so as to address disease-gene activity not currently addressed by the treatment or treatments in the original or existing treatment.

22. The method of claim 21, wherein each said treatment is selected from the group consisting of: a drug, a combination of drugs, a compound, a combination of compounds, radiation, a genetic sequence, a combination of genetic sequences, heat, cryogenics and a combination of two or more of any of the previous members in this group.

23. The method of claim 21, further comprising the steps of:
- labeling the phenotypic/genotypic signatures representing the differential expression levels as "in phase" signatures;
- generating "out of phase" signatures by inverting the "in phase" signatures; and
- including the "out of phase" signatures with the "in phase" signatures and the treatment-response signatures when performing steps (j) and (k).

24. A method for screening a combination of treatments to specifically target a disease process, wherein the disease process impacts gene expression, said method comprising the steps of:
- (a) providing differential expression levels of predetermined genes of diseased tissue samples relative to at least one reference tissue for respective features of microarrays targeting the predetermined genes used to calculate the differential expression levels;
- (b) for each of the respective features of respective microarrays for each diseased tissue sample, providing a single phenotypic/genotypic signature as a vector representing the differential expression level for each diseased tissue sample for that feature across the respective microarrays;
- (c) treating the diseased tissue samples with a treatment;
- (d) measuring a treatment-response value with respect to each of the diseased tissue samples as effected by the treatment;
- (e) generating a single phenotypic signature as a response vector representing the treatment-response values of each of the diseased tissue samples;
- (f) repeating steps (c)-(e) with a different treatment at least once so that multiple phenotypic signatures have been generated for multiple treatments;
- (g) performing a clustering operation based on the phenotypic/genotypic signatures of the differential expression levels and the phenotypic signatures of the treatment-response values together;
- (h) selecting treatments by identifying the treatment-response phenotypic signatures caused by those treatments, and which are clustered with phenotypic/genotypic signatures representing differential expression levels representative of the diseased tissue samples;
- (i) labeling the phenotypic/genotypic signatures representing the differential expression levels as "in phase" signatures;
- (j) generating "out of phase" signatures by inverting the "in phase" signatures; and
- (k) including the "out of phase" signatures with the "in phase" signatures and the treatment-response signatures when performing steps (g) and (h).

25. A method of augmenting an original or existing single treatment or treatment combination for a disease with at least one additional treatment that covers gene activity of the disease not addressed by the original or existing treatment, said method comprising the steps of:
- (a) providing differential expression levels of predetermined genes of diseased tissue samples relative to at least one reference tissue for respective features of microarrays targeting the predetermined genes used to calculate the differential expression levels;
- (b) for each of the respective features of respective microarrays for each diseased tissue sample, providing a phenotypic/genotypic signature as a vector representing the differential expression level for each diseased tissue sample for that feature across the respective microarrays;
- (c) treating the diseased tissue samples with the original or existing single treatment or combination treatment;
- (d) measuring a treatment-response value with respect to each of the diseased tissue samples as effected by the original or existing single or combination treatment;
- (e) generating a phenotypic signature as a vector representing the treatment-response values of each of the diseased tissue samples as effected by the original or existing single or combination treatment;
- (f) treating the diseased tissue samples with a treatment that is not included in the original or existing single or combination treatment;
- (g) measuring a treatment-response value with respect to each of the diseased tissue samples as effected by the treatment that is not included in the original or existing single or combination treatment;
- (h) generating a phenotypic signature as a vector representing the treatment-response values of each of the diseased tissue samples as effected by the treatment that is not included in the original or existing single or combination treatment;
- (i) repeating steps (f)-(h) with a different treatment that is also not included in the original or existing single or combination treatment at least once so that multiple phenotypic signatures have been generated for multiple treatments not included in the original or existing single or combination treatment;
- (j) performing a clustering operation based on the phenotypic/genotypic signatures of the differential expression levels and the phenotypic signatures of the treatment-response values together;
- (k) selecting at least one treatment by identifying the treatment-response phenotypic signatures caused by the at least one treatment, and which are clustered with phenotypic signatures identifying the treatment-response phenotypic signatures caused by the treatment or treatments in the original treatment, as well as with phenotypic/genotypic signatures representing differential expression levels representative of the diseased tissue samples, but separated from the phenotypic signatures identifying the treatment-response phenotypic signatures caused by the treatment or treatments in the original treatment, so as to address disease-gene activity not currently addressed by the treatment or treatments in the original or existing treatment;
- labeling the phenotypic/genotypic signatures representing the differential expression levels as "in phase" signatures;
- generating "out of phase" signatures by inverting the "in phase" signatures; and
- including the "out of phase" signatures with the "in phase" signatures and the treatment-response signatures when performing steps (j) and (k).

* * * * *

UNITED STATES PATENT AND TRADEMARK OFFICE
CERTIFICATE OF CORRECTION

PATENT NO. : 7,348,144 B2
APPLICATION NO. : 10/640081
DATED : March 25, 2008
INVENTOR(S) : Minor It is certified that error appears in the above-identified patent and that said Letters Patent is hereby corrected as shown below:

In column 18, line 48, in Claim 1, delete "phenotypic/genotypic" and insert -- phenotypic --, therefor.

In column 18, lines 49-50, in Claim 1, delete "phenotypic" and insert -- phenotypic/genotypic --, therefor.

In column 19, lines 31, in Claim 11, delete "9," and insert -- 10, --, therefor.

Signed and Sealed this

Nineteenth Day of August, 2008

JON W. DUDAS
*Director of the United States Patent and Trademark Office*